US009987451B2

(12) United States Patent
Stegman

(10) Patent No.: US 9,987,451 B2
(45) Date of Patent: Jun. 5, 2018

(54) CUSHION WITH SELECTIVELY VARIABLE SOFTNESS/STIFFNESS

(71) Applicant: KONINKLIJKE PHILIPS N.V., Eindhoven (NL)

(72) Inventor: Steven Charles Stegman, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 709 days.

(21) Appl. No.: 14/348,622

(22) PCT Filed: Sep. 27, 2012

(86) PCT No.: PCT/IB2012/055157
§ 371 (c)(1),
(2) Date: Mar. 31, 2014

(87) PCT Pub. No.: WO2013/050911
PCT Pub. Date: Apr. 11, 2013

(65) Prior Publication Data
US 2014/0283832 A1    Sep. 25, 2014

(51) Int. Cl.
*A61M 16/06* (2006.01)
*A61M 16/00* (2006.01)
*A61M 16/08* (2006.01)

(52) U.S. Cl.
CPC .... *A61M 16/0622* (2014.02); *A61M 16/0003* (2014.02); *A61M 16/0051* (2013.01);
(Continued)

(58) Field of Classification Search
CPC .. A61M 16/00; A61M 16/0003; A61M 16/06; A61M 16/0605; A61M 16/0611; A61M 16/0616; A61M 16/0622; A61M 16/0627; A61M 16/0633; A61M 2016/0661; A62B 18/00; A62B 18/02
See application file for complete search history.

(56) References Cited

U.S. PATENT DOCUMENTS

| 5,560,354 A * | 10/1996 | Berthon-Jones ...... A61M 16/06 128/204.18 |
| 6,494,206 B1 * | 12/2002 | Bergamaschi ........ A61M 16/06 128/206.21 |

(Continued)

FOREIGN PATENT DOCUMENTS

| CN | 101861180 A | 10/2010 |
| CN | 101969871 A | 2/2011 |

(Continued)

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

A cushion (16) for use with a mask (10) in delivering a flow of breathing gas to a user includes a first portion adapted to contact a surface of a user, a second portion adapted to be coupled to a mask shell (18), and a wall portion extending between the first portion and the second portion. The wall portion includes a chamber formed therein, the chamber having one of an electro-rheological fluid or a magneto-rheological fluid disposed therein. The cushion further includes a means (44, 50) for selectively varying the apparent viscosity of the fluid disposed within the chamber.

15 Claims, 4 Drawing Sheets

(52) U.S. Cl.
CPC ........ *A61M 16/0057* (2013.01); *A61M 16/06* (2013.01); *A61M 16/0633* (2014.02); *A61M 16/0605* (2014.02); *A61M 16/0683* (2013.01); *A61M 16/0816* (2013.01); *A61M 2016/0661* (2013.01); *A61M 2205/0288* (2013.01)

(56) References Cited

U.S. PATENT DOCUMENTS

| | | |
|---|---|---|
| 7,066,179 B2 | 6/2006 | Eaton |
| 8,276,588 B1 * | 10/2012 | Connor ................. A61M 16/06 128/205.25 |
| 2003/0088906 A1 * | 5/2003 | Baker ................. A42B 3/0473 2/416 |
| 2004/0113404 A1 | 6/2004 | Ryan |
| 2006/0185675 A1 * | 8/2006 | Colin ................... A61M 16/06 128/206.24 |
| 2007/0043306 A1 | 2/2007 | Olson |
| 2007/0095349 A1 | 5/2007 | Hansmann |
| 2007/0163594 A1 * | 7/2007 | Ho ....................... A61M 16/06 128/206.24 |
| 2008/0083412 A1 | 4/2008 | Henry |
| 2008/0306419 A1 | 12/2008 | Bishop |
| 2009/0211595 A1 | 8/2009 | Sinha |
| 2009/0255023 A1 | 10/2009 | Williams |
| 2010/0006100 A1 * | 1/2010 | Eifler .................... A61M 16/06 128/206.24 |
| 2010/0024811 A1 * | 2/2010 | Henry ................... A61M 16/06 128/202.16 |
| 2010/0119755 A1 | 5/2010 | Chung |
| 2011/0220112 A1 * | 9/2011 | Connor ................. A61M 16/06 128/206.24 |
| 2012/0132208 A1 * | 5/2012 | Judson .............. A61M 16/0622 128/205.25 |
| 2013/0019384 A1 * | 1/2013 | Knight ................... A42B 3/064 2/411 |

FOREIGN PATENT DOCUMENTS

| | | |
|---|---|---|
| WO | WO2009062265 A1 | 5/2009 |
| WO | WO2009093174 A1 | 7/2009 |
| WO | WO2011003128 A1 | 1/2011 |
| WO | WO2011073814 A1 | 6/2011 |

* cited by examiner

CUSHION WITH SELECTIVELY VARIABLE SOFTNESS/STIFFNESS

CROSS REFERENCE TO RELATED APPLICATIONS

This patent application claims the priority benefit under 35 U.S.C. § 371 of international patent application no. PCT/IB2012/055157, filed Sep. 27, 2012, which claims the priority benefit under 35 U.S.C. § 119(e) of U.S. Provisional Application No. 61/542,412 filed on Oct. 3, 2011, the contents of which are herein incorporated by reference.

BACKGROUND OF THE INVENTION

1. Field of the Invention

The present invention generally relates to a cushion for use on a patient interface device in a pressure support system that supplies a flow of gas to the airway of a patient, and, more particularly, to a cushion in which at least a portion of the cushion has a viscosity (softness/stiffness) that can be selectively varied by the user.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort. A problem arises in that in order for the mask to maintain a seal without any undue gas leaks around the periphery of the mask, the mask may be compressed against the patient's face.

Conventional CPAP mask cushion technology provides for a relatively constant force along the perimeter of the cushion where the cushion contacts the face. When the mask, and thus the cushion, moves relative to the face, a gap can occur that allows air to leak between the cushion and the face. Such gap occurs due to the inability of the cushion to change its contour to match that of the patient's face. This inability is directly proportional to the stiffness of the cushion. Conventional cushions must provide a level of support along with sealing capability. Conventional masks attempt to vary the stiffness around the cushion perimeter by varying the cross section of the cushion walls. While such designs have shown promise, there is still room for improvement.

SUMMARY OF THE INVENTION

Accordingly, it is an object of the present invention to provide an improved cushion for use in a patient interface device that overcomes the shortcomings of conventional cushions. As an aspect of the invention, a cushion is provided that comprises a first portion adapted to contact a surface of a user; a second portion adapted to be coupled to a mask shell; and a wall portion extending between the first portion and the second portion. The wall portion includes a chamber formed therein, the chamber having one of an electro-rheological fluid or a magneto-rheological fluid disposed therein. The cushion further comprises a means for selectively varying the apparent viscosity of the fluid disposed within the chamber.

The chamber may include an electro-rheological fluid disposed therein and the means for selectively varying the apparent viscosity of the fluid may comprise a pair of electrodes in communication with the fluid.

The chamber may include a magneto-rheological fluid disposed therein and the means for selectively varying the stiffness of the fluid may comprise a source for producing a magnetic field. The source for producing a magnetic field may comprise an electromagnet disposed on, or proximate to, the cushion.

The wall portion may further include a second chamber separate from the first chamber, the second chamber having a fluid or gel material disposed therein. The second chamber may include one of an electro-rheological fluid or a magneto-rheological fluid disposed therein and the means for selectively varying the stiffness of the fluid may include a means for selectively varying the stiffness of the fluid disposed within the second chamber.

As another aspect of the invention, a patient interface device is provided. The patient interface devices comprises a mask shell adapted to receive a flow of breathing gas and a cushion. The cushion comprises: a first portion adapted to contact a surface of a user; a second portion coupled to the mask shell; and a wall portion extending between the first portion and the second portion. The wall portion includes a chamber formed therein, the chamber having one of an electro-rheological fluid or a magneto-rheological fluid disposed therein. The cushion further comprises a means for selectively varying the apparent viscosity of the fluid disposed within the chamber.

The chamber may include an electro-rheological fluid disposed therein and the means for selectively varying the apparent viscosity of the fluid may comprise a pair of electrodes in communication with the fluid.

The chamber may include a magneto-rheological fluid disposed therein and the means for selectively varying the stiffness of the fluid may comprise a source for producing a magnetic field. The source for producing a magnetic field may comprise an electromagnet disposed on, or proximate to, the cushion.

The wall portion may further include a second chamber separate from the first chamber, the second chamber having a fluid or gel material disposed therein. The second chamber may include one of an electro-rheological fluid or a magneto-rheological fluid disposed therein, and the means for selectively varying the stiffness of the fluid may include a means for selectively varying the stiffness of the fluid disposed within the second chamber.

As yet another aspect of the invention, a system for providing a pressurized flow of gas to the airway of a patient is provided. The system comprises: a pressure/flow generating system; a mask shell coupled to the pressure/flow generating system via a conduit; and a cushion. The cushion comprises: a first portion adapted to contact a surface of a user, a second portion coupled to the mask shell, and a wall portion extending between the first portion and the second portion. The wall portion includes a chamber formed therein, the chamber having one of an electro-rheological fluid or a magneto-rheological fluid disposed therein. The system further comprises a means for selectively varying the apparent viscosity of the fluid disposed in the chamber and a switchable power source electrically coupled to the means for selectively varying the apparent viscosity of the fluid disposed in the chamber. The switchable power source may comprise a processing means adapted to detect a leak of pressurized gas within the system and responsive thereto, selectively vary the apparent viscosity of the fluid disposed in the chamber.

Figure 1:
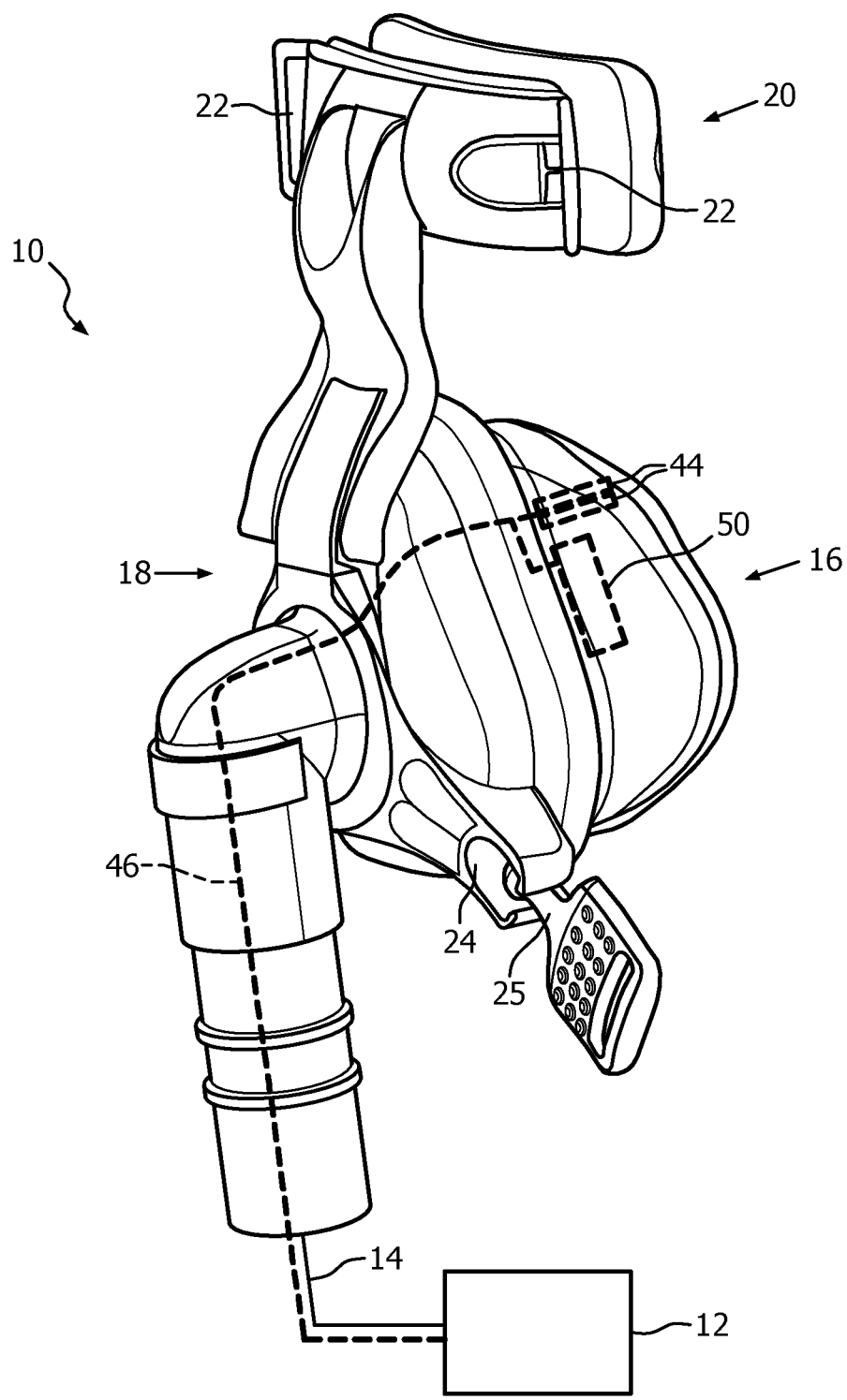
FIG. 1 is a front isometric view of a patient interface device according to the principles of the present invention shown (schematically) connected to a gas flow/pressure generating system to form a patient interface system.
Figure 2:
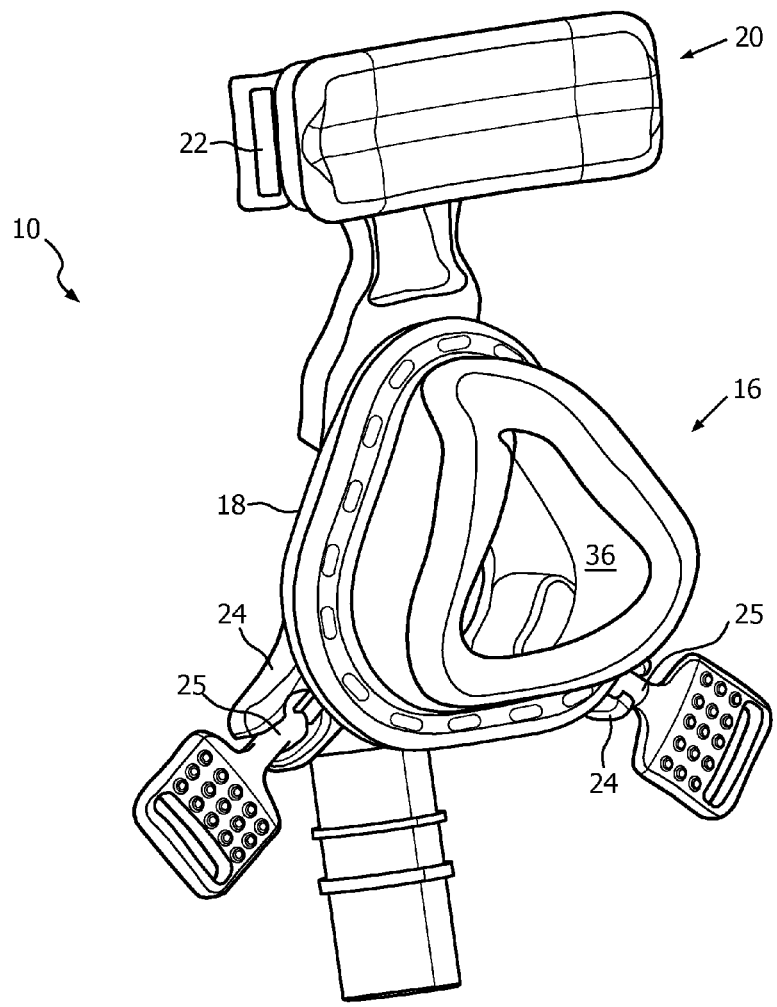
FIG. 2 is a rear isometric view of the patient interface device of FIG. 1.
Figure 5:
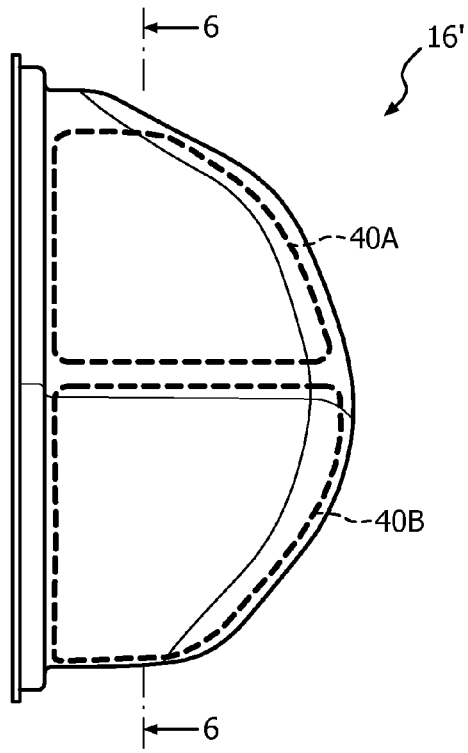
Figure 6:
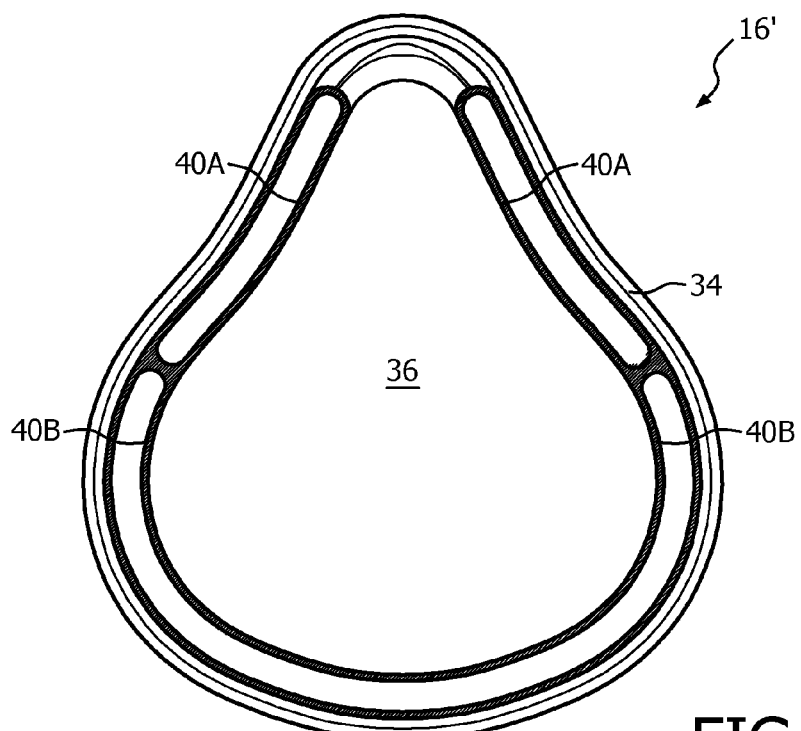

rear, user side, isometric view of another cushion according to the principles of the present invention;

FIG. 5 is a side view of another cushion in accordance with the principles of the present invention for use in a patient interface device such as shown in of FIGS. 1 and 2; and FIG. 6 is a sectional view of the cushion of FIG. 5 taken along line 6-6 of FIG. 5.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIGS. 1-4 illustrate an exemplary embodiment of a patient interface device 10 and components thereof according to the principles of the present invention. Patient interface device 10 communicates a flow of breathing gas between the patient's airway and a pressure/flow generating system 12 (shown schematically), such as a ventilator, CPAP device, or variable pressure device, e.g., a BiPAP® device manufactured and distributed by Respironics, Inc. of Pittsburgh, Pa., or an auto-titration pressure support system.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating system 12 is also referred to as a gas flow generating device, because flow results when a pressure gradient is generated. The present invention contemplates that pressure/flow generating system 12 is any conventional system for delivering a flow of gas to an airway of a patient or for elevating a pressure of gas at an airway of the patient, including the pressure support systems summarized above and non-invasive ventilation systems.

Communicating a flow of breathing gas between the patient's airway and pressure/flow generating system 12 includes delivering a flow of breathing gas to the patient from the pressure/flow generating device and exhausting a flow of gas from the patient to ambient atmosphere. The system for delivering a breathing gas to a patient according to the present invention comprises the pressure/flow generating system that produces a flow of gas, and a conduit 14, which is also referred to as a patient circuit, having a first end portion (not numbered) operatively coupled to the gas flow generating device and a second end portion (not numbered). Conduit 14 carries the flow of gas from pressure/flow generating device 12 during operation of the system to patient interface device 10, which is coupled to the second end portion of the conduit. Conduit 14 corresponds to any conduit suitable for communicating the flow of gas form the pressure/flow generating system to the patient interface device. A typical conduit is a flexible tube. A headgear assembly, which is not shown in the figures, attaches patient interface device 10 to the patient's head.

Patient interface device 10 includes a cushion, generally indicated at 16, and a mask shell 18 having a patient side and opposite thereto, an outer side. Attached to outer side of mask shell 18 is a conduit coupling member (not numbered) that couples mask shell 18 to conduit 14 so that a flow of gas is communicated to the interior of the patient interface device for subsequent delivery to the patient. Conversely, gas from the patient is communicated from the patient interface device into conduit 14, where an exhaust port is located. Mask shell 18 is preferably a generally rigid shell, and, in an exemplary embodiment of the present invention is formed from rigid plastic, such as polycarbonate. It is to be understood that the present invention contemplates that one or more of the size, shape, or composition of mask shell 18 may be varied without varying from the scope of the present invention.

In the illustrated embodiment of FIG. 1, mask shell 18 has a generally triangular shape having a forehead support portion 20 that includes headgear attaching elements in the form of receiving holes or slots 22 disposed on either side of forehead support portion 20 for receiving headgear straps (not illustrated). In the illustrated embodiment, the lower corners of mask shell 18 also include headgear attaching elements in the form of socket attachment elements 24, which cooperate with corresponding ball elements 25 on headgear straps (not illustrated). The ball and socket configuration, and other headgear attachment configurations suitable for use with the present invention, are disclosed, for example, without limitation, in commonly assigned U.S. Pat. No. 7,066,179, the contents of which are incorporated herein by reference.

It is to be understood that the present invention contemplates using any conventional connection assembly to attach a headgear or headgear strap to mask shell 18 or other suitable shell arrangement. It is to be further understood that the present invention also contemplates eliminating the forehead support entirely, so that the patient interface device is supported on the patient by cushion 16. If the forehead support is eliminated, a headgear attachment may be provided at the upper apex of the mask shell. The present invention also contemplates providing a post or other protrusion at the upper portion of the shell, i.e., the portion overlying the bridge of the nose, to which the headgear can be attached.

The present invention contemplates that the headgear suitable for use with patient interface device 10 is any conventional headgear used in the patient interface field. For example, without limitation, a typical headgear assembly comprises a headpiece that overlies a portion of the patient's crania and with headgear straps extending therefrom to adjustably connect the headgear to the mask.

Figure 3:
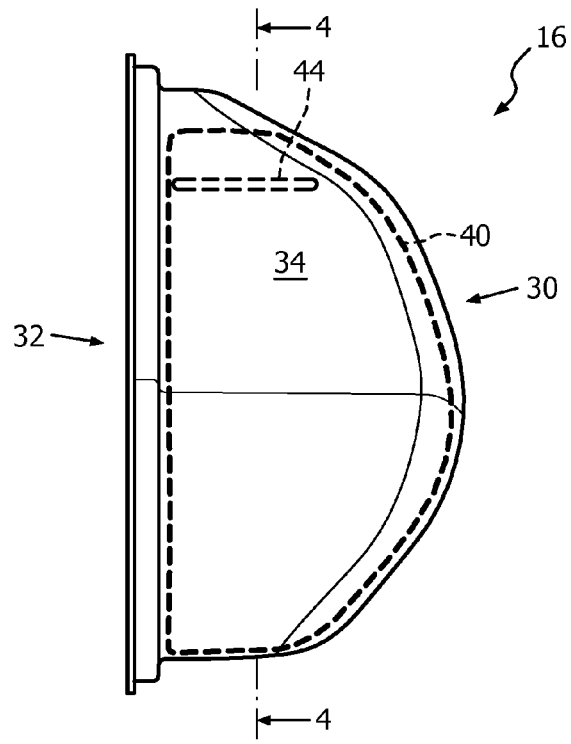
FIG. 3 is a side view of the cushion of the patient interface device of FIGS. 1 and 2.
Figure 4:
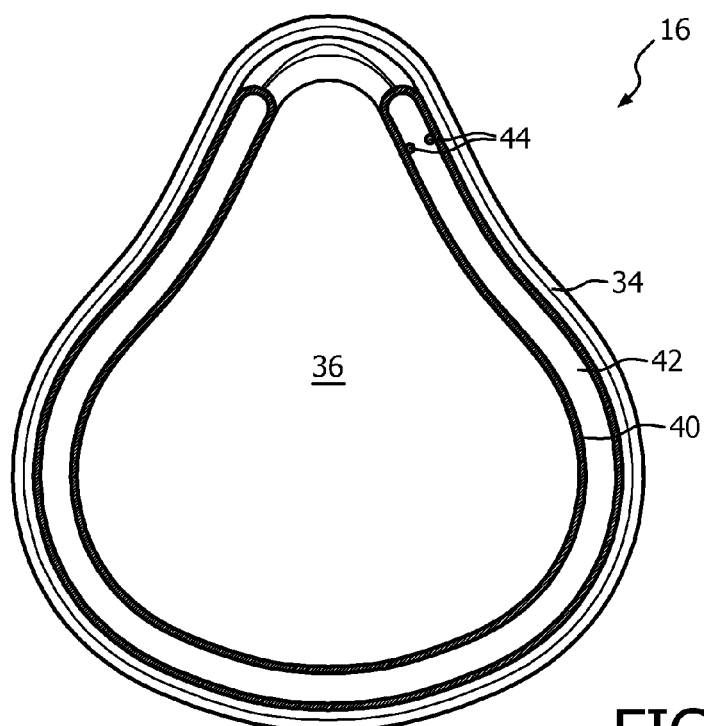
FIG. 4 is a sectional view of the cushion of the patient interface device of FIGS. 1 and 2 taken along line 4-4 of FIG. 3.

Referring to FIGS. 3 and 4, cushion 16 is preferably formed of a soft, cushiony, elastomeric material, such as silicone, appropriately soft thermoplastic elastomers, closed cell foam, thin materials, or any combination of suitable materials. Cushion 16 has a first end portion 30 adapted to sealingly engage an inner perimeter of the face of a user, a second end portion 32 generally opposite first end portion 30 that is adapted to be coupled to a mask (such as mask 18 in FIGS. 1 and 2), and a wall portion 34 extending between first end portion 30 and second end portion 32. A nose receiving cavity 36 (FIGS. 2 and 4) adapted to receive at least a portion of a user's nose is defined in the interior of cushion 16 by wall portion 34. As shown in FIGS. 3 and 4, wall portion 34 includes a sealed chamber 40 formed therein. Disposed within sealed chamber 40 is a fluid having an apparent viscosity (softness/stiffness) that can be selectively controlled, such as an electro-rheological (ER) fluid, 42.

As known in the art, electro-rheological (ER) fluids are suspensions of extremely fine non-conducting particles (typically up to 50 micrometers diameter) disposed in an electrically insulating fluid. The apparent viscosity of these fluids (and thus the softness/stiffness) changes reversibly by an order of up to 100,000 in response to an electric field. As an example, a typical ER fluid can go from the consistency of a liquid to that of a gel, and back, with response times on the order of milliseconds responsive to the presence and subsequent removal of an electric field. By varying the apparent viscosity of electro-rheological fluid 42 disposed within sealed chamber 40, the stiffness of cushion 16 may be varied.

The change in apparent viscosity of electro-rheological fluid 42 is dependent on the applied electric field, i.e. the potential divided by the distance between the electrodes through which the electric field is applied. The change is not a simple change in viscosity, hence these fluids are now known as ER fluids, rather than by the older term Electro Viscous fluids. The effect is better described as an electric field dependent shear yield stress. When activated, an ER fluid behaves as a Bingham plastic (a type of viscoelastic material), with a yield point which is determined by the electric field strength. After the yield point is reached, the fluid shears as a fluid, i.e. the incremental shear stress is proportional to the rate of shear (in a Newtonian fluid there is no yield point and stress is directly proportional to shear). Hence the resistance to motion of the fluid can be controlled by adjusting the applied electric field.

In order to vary the apparent viscosity of the electro-rheological fluid 42, a number of electrodes 44 (two are shown schematically for example purposes in FIG. 4) are provided in electrical communication with electro-rheological fluid 42. Although only two electrodes 44 are shown in FIG. 4, it is to be appreciated that, dependent on the application, several pairs of electrodes would be spaced throughout sealed chamber 40. Preferably, electrodes 44 are formed from thin gage wires or other suitable flexible materials that are generally embedded in, or coupled to, walls of sealed chamber 40. FIGS. 3 and 4 show a schematic representation of one potential arrangement of a pair of electrodes 44, however, it is to be understood that the present invention contemplates that one or more of the shape, quantity, or placement of individual electrodes may be varied without varying from the scope of the present invention. For example, by varying the spacing of electrodes in different portions of sealed chamber 40, the apparent viscosity of electro-rheological fluid 42 may be varied in particular areas of interest within sealed chamber 40.

In order to provide an electrical current to electro-rheological fluid 42, electrodes 44 are electrically coupled to a switchable power source. As shown in FIG. 1, pressure/flow generating system 12 may be utilized as such a power source and electrodes 44 may be coupled thereto via wires 46 disposed along, or formed integrally therewith, conduit 14. In such arrangement, current to the electrodes, and thus the stiffness of cushion 16, may be varied manually by a user or operator, or may be controlled via an automated process or system. An example of such system is disclosed, for example, without limitation, in commonly assigned International Publication WO 2011/073814 A1, the contents of which are incorporated herein by reference. Alternatively, a switchable power source in electrical communication with electrodes 44 may be provided directly on one of the cushion 16 or mask 18. It is to be understood that the present invention contemplates that the power source utilized may be an AC source, such as would most likely be provided by pressure/flow generating system 12 or that the power source may be a DC source, such as provided by batteries or other suitable means that may be provided as part of the pressure/flow generating system, on the mask, on the cushion, or at any other suitable location.

As an alternative to electro-rheological fluid 42, a magneto-rheological fluid may instead be employed within sealed chamber 40. As known in the art, a magneto-rheological fluid (MR fluid) is a type of smart fluid in a carrier fluid, usually a type of oil. When subjected to a magnetic field, the fluid greatly increases its apparent viscosity, to the point of becoming a viscoelastic solid. Importantly, the yield stress of the fluid when in its active ("on") state can be controlled very accurately by varying the magnetic field intensity. Accordingly, instead of electrodes 44, embodiments employing an MR fluid would instead preferably employ one or more electromagnets 50 disposed on or near cushion 16 or mask 18, such as shown schematically in phantom line in FIG. 1. Like electrodes 44 previously discussed, each electromagnet 50 may be electrically coupled to pressure/flow generating system 12 (such as, without limitation, by wires 46) or may be powered by a power source also provided on one of mask 18 or cushion 16.

FIGS. 5 and 6, respectively, show side and cross-sectional views of a cushion 16' in accordance with another embodiment of the present invention which utilizes multiple sealed chambers 40A and 40B, instead of a single sealed chamber 40. Each of upper chambers 40A and lower chamber 40B may be filled with either of an electro-rheological or magneto-rheological fluid, thus allowing the stiffness of the upper and lower portions of cushion 16' to be independently adjusted utilizing the principles previously discussed in regard to the embodiment shown in FIGS. 1-4. Although shown has having a total of three compartments disposed in upper and lower portions of mask 16', it is to be appreciated that the present invention contemplates that the quantity and/or relative positioning of multiple sealed chambers may be varied without varying from the scope of the present invention. It is also to be appreciated that the present invention contemplates that sealed chambers containing electro or magneto-rheological fluids may also be employed in conjunction with sealed chambers containing materials of non-varying stiffness without varying from the scope of the present invention.

It is to be appreciated that the invention improves seal between a cushion and a patient's face by providing the ability to adjust the stiffness of all, or selected portions of, the cushion. Additionally, the invention allows for such adjustments to be made upon initial set-up or to be made dynamically in response to detected leaks or other triggers.

It is to be appreciated that the present invention is intended to be limited to the mask or cushion shapes described herein but instead may be employed with masks and cushion of various other shapes or designs.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for use in delivering a flow of breathing gas to the airway of a patient, the cushion comprising:
    a first portion having a non-planar contoured surface which is adapted to contact a face of the patient;
    a second portion adapted to be coupled to a mask shell;
    a wall portion extending between the first portion and the second portion, the wall portion extending continuously around a cavity defined thereby which extends between the first portion and the second portion and is adapted to receive a portion of the face of the user, the wall portion including a sealed chamber formed therein;
    a fluid disposed in the sealed chamber, wherein an apparent viscosity of the fluid is selectively variable; and
    a means for selectively varying the apparent viscosity of the fluid disposed within the sealed chamber.

2. The cushion of claim 1, wherein the fluid is an electro-rheological fluid or a magneto-rheological fluid disposed in the chamber.

3. The cushion of claim 2, wherein the means for selectively varying the apparent viscosity of the fluid comprises a pair of electrodes in communication with the fluid or a source for producing a magnetic field.

4. The cushion of claim 3, wherein the source for producing a magnetic field comprises an electromagnet disposed on, or proximate to, the cushion.

5. The cushion of claim 1, wherein the sealed chamber comprises a first sealed chamber, and wherein the wall portion further includes a second sealed chamber separate from the first sealed chamber, the second sealed chamber having a fluid or gel material disposed therein.

6. The cushion of claim 5, wherein the second chamber includes one of an electro-rheological fluid or a magneto-rheological fluid disposed therein, and wherein the means for selectively varying the apparent viscosity of the fluid includes means for selectively varying the apparent viscosity of the fluid disposed within the second chamber.

7. A patient interface device for use in delivering a flow of breathing gas to the airway of a patient, interface device comprising:
    a mask shell adapted to receive a flow of breathing gas; and
    a cushion as recited in claim 1.

8. The patient interface device of claim 7, wherein the fluid is an electro-rheological fluid or a magneto-rheological fluid disposed in the chamber.

9. The patient interface device of claim 8, wherein the means for selectively varying the apparent viscosity of the fluid comprises a pair of electrodes in communication with the fluid or a source for producing a magnetic field.

10. The patient interface device of claim 9, wherein the source for producing a magnetic field comprises an electromagnet disposed on, or proximate to, the cushion.

11. The patient interface device of claim 7, wherein the sealed chamber comprises a first sealed chamber, and wherein the wall portion further includes a second sealed chamber separate from the first sealed chamber, the second sealed chamber having a fluid or gel material disposed therein.

12. The patient interface device of claim 11, wherein the second chamber includes one of an electro-rheological fluid or a magneto-rheological fluid disposed therein, and wherein the means for selectively varying the apparent viscosity of the fluid includes a means for selectively varying the apparent viscosity of the fluid disposed within the second chamber.

13. A system for providing a pressurized flow of gas to the airway of a patient, the system comprising:
   a pressure/flow generating system;
   a mask shell coupled to the pressure/flow generating system via a conduit;
   a cushion as recited in claim 1; and
   a switchable power source electrically coupled to the means for selectively varying the apparent viscosity of the fluid disposed in the sealed chamber.

14. The system of claim 13, wherein the fluid is an electro-rheological fluid or a magneto-rheological fluid disposed in the chamber.

15. The system of claim 13, wherein the switchable power source comprises a processing means adapted to detect a leak of pressurized gas within the system and responsive thereto, selectively vary the apparent viscosity of the fluid disposed in the sealed chamber.

\* \* \* \* \*